(12) United States Patent
Boukhny et al.

(10) Patent No.: US 8,157,797 B2
(45) Date of Patent: Apr. 17, 2012

(54) CAPSULARHEXIS DEVICE WITH RETRACTABLE BIPOLAR ELECTRODES

(75) Inventors: Mikhail Boukhny, Laguna Niguel, CA (US); James Chon, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 506 days.

(21) Appl. No.: 12/351,898

(22) Filed: Jan. 12, 2009

(65) Prior Publication Data
US 2010/0179544 A1    Jul. 15, 2010

(51) Int. Cl.
*A61B 18/18*    (2006.01)
(52) U.S. Cl. ............... 606/45; 606/47; 606/48
(58) Field of Classification Search .......... 606/48, 606/49, 32, 37, 39, 41, 45, 113
See application file for complete search history.

(56) References Cited

U.S. PATENT DOCUMENTS

| | | |
|---|---|---|
| 3,159,161 A | 12/1964 | Ness |
| 3,809,093 A | 5/1974 | Abraham |
| 3,844,272 A | 10/1974 | Banko |
| 3,915,172 A | 10/1975 | Wichterle et al. |
| 3,949,750 A | 4/1976 | Freeman |
| 4,002,169 A | 1/1977 | Cupler, II |
| 4,026,295 A | 5/1977 | Lieberman |
| 4,068,664 A | 1/1978 | Sharp et al. |
| 4,210,146 A | 7/1980 | Banko |
| 4,301,802 A | 11/1981 | Poler |
| 4,367,744 A | 1/1983 | Sole |
| 4,368,734 A | 1/1983 | Banko |
| 4,457,757 A | 7/1984 | Molteno |
| 4,481,948 A | 11/1984 | Sole |
| 4,501,274 A | 2/1985 | Skjaerpe |
| 4,530,356 A | 7/1985 | Helfgott et al. |
| 4,530,359 A | 7/1985 | Helfgott et al. |
| 4,531,934 A | 7/1985 | Kossovsky et al. |
| 4,559,942 A | 12/1985 | Eisenberg |
| 4,570,632 A | 2/1986 | Woods |
| 4,607,622 A | 8/1986 | Fritch et al. |
| 4,676,243 A | 6/1987 | Clayman |
| 4,706,669 A | 11/1987 | Schlegel |
| 4,708,138 A | 11/1987 | Pazandak |
| 4,729,761 A | 3/1988 | White |
| 4,766,896 A | 8/1988 | Pao |

(Continued)

FOREIGN PATENT DOCUMENTS

DE    3038024 A1    4/1982
(Continued)

OTHER PUBLICATIONS

Bretton, Randolph H. et al., "Use of bipolar diathermy to prevent posterior capsule opacification," Journal of Cataract Refractive Surgery 2002; 2 8:866-878.

(Continued)

*Primary Examiner* — Laura Bouchelle

(57) ABSTRACT

A capsularhexis device includes a loop-shaped cutting portion formed from flexible, superelastic metal strips separated by an insulating layer, and configured so that the cutting portion may be retracted into a tubular insertion cartridge for insertion into and removal from the eye, and extended from the insertion cartridge for the capsularhexis procedure. In its extended configuration, the cutting portion forms a cutting loop such that a free end of the cutting loop is proximate a connecting end of the cutting loop, with the connecting end joined to a shaft portion. The shaft portion extends into the insertion capsule, and is used to move the cutting portion in and out of the insertion cartridge.

11 Claims, 4 Drawing Sheets

U.S. PATENT DOCUMENTS

| | | | |
|---|---|---|---|
| 4,766,897 A | 8/1988 | Smirmaul | |
| 4,781,675 A | 11/1988 | White | |
| 4,805,616 A | 2/1989 | Pao | |
| 4,869,716 A | 9/1989 | Smirmaul | |
| 4,885,004 A | 12/1989 | Pao | |
| 4,900,300 A | 2/1990 | Lee | |
| 4,911,161 A | 3/1990 | Schechter | |
| 4,936,825 A | 6/1990 | Ungerleider | |
| 4,950,272 A | 8/1990 | Smirmaul | |
| 4,955,859 A | 9/1990 | Zilber | |
| 4,955,894 A | 9/1990 | Herman | |
| 4,986,825 A | 1/1991 | Bays et al. | |
| 4,994,066 A | 2/1991 | Voss | |
| 5,047,008 A | 9/1991 | de Juan, Jr. et al. | |
| 5,085,664 A | 2/1992 | Bozzo | |
| 5,123,906 A | 6/1992 | Kelman | |
| 5,135,530 A | 8/1992 | Lehmer | |
| 5,180,362 A | 1/1993 | Worst | |
| 5,188,634 A | 2/1993 | Hussein et al. | |
| 5,199,445 A | 4/1993 | Rubinfeld | |
| 5,203,865 A | 4/1993 | Siepser | |
| 5,234,436 A | 8/1993 | Eaton et al. | |
| 5,242,404 A | 9/1993 | Conley et al. | |
| 5,242,449 A | 9/1993 | Zaleski | |
| 5,261,923 A | 11/1993 | Soares | |
| 5,269,787 A | 12/1993 | Cozean, Jr. et al. | |
| 5,322,504 A | 6/1994 | Doherty et al. | |
| 5,342,377 A | 8/1994 | Laszerson | |
| 5,346,491 A | 9/1994 | Oertli | |
| 5,360,399 A | 11/1994 | Stegmann | |
| 5,364,405 A | 11/1994 | Zaleski | |
| 5,374,244 A | 12/1994 | Clement et al. | |
| 5,395,361 A | 3/1995 | Fox et al. | |
| 5,411,510 A | 5/1995 | Fugo | |
| 5,413,574 A | 5/1995 | Fugo | |
| 5,423,330 A | 6/1995 | Lee | |
| 5,423,841 A | 6/1995 | Kornefeld | |
| 5,439,474 A | 8/1995 | Li | |
| 5,466,234 A | 11/1995 | Loeb et al. | |
| 5,478,338 A | 12/1995 | Reynard | |
| 5,484,433 A | 1/1996 | Taylor et al. | |
| 5,486,165 A | 1/1996 | Stegmann | |
| 5,487,725 A | 1/1996 | Peyman | |
| 5,522,829 A | 6/1996 | Michalos | |
| 5,527,332 A | 6/1996 | Clement | |
| 5,562,692 A | 10/1996 | Bair | |
| 5,569,197 A | 10/1996 | Helmus et al. | |
| 5,569,280 A | 10/1996 | Kamerling | |
| 5,601,094 A | 2/1997 | Reiss | |
| 5,601,593 A | 2/1997 | Freitag | |
| 5,626,558 A | 5/1997 | Suson | |
| 5,630,827 A | 5/1997 | Vijfvinkel | |
| 5,651,783 A | 7/1997 | Reynard | |
| 5,662,670 A | 9/1997 | Michalos | |
| 5,669,923 A | 9/1997 | Gordon | |
| 5,670,161 A | 9/1997 | Healy et al. | |
| 5,683,592 A | 11/1997 | Bartholomew et al. | |
| 5,700,243 A | 12/1997 | Narciso, Jr. | |
| 5,716,363 A | 2/1998 | Josephberg | |
| 5,728,117 A | 3/1998 | Lash | |
| 5,733,297 A | 3/1998 | Wang | |
| 5,741,244 A | 4/1998 | Klaas | |
| 5,755,731 A | 5/1998 | Grinberg | |
| 5,766,171 A * | 6/1998 | Silvestrini | 606/49 |
| 5,792,166 A | 8/1998 | Gordon et al. | |
| 5,827,321 A | 10/1998 | Roubin et al. | |
| 5,860,994 A | 1/1999 | Yaacobi | |
| 5,868,697 A | 2/1999 | Richter et al. | |
| 5,873,883 A | 2/1999 | Cozean, Jr. et al. | |
| 5,888,201 A | 3/1999 | Stinson et al. | |
| 5,891,084 A | 4/1999 | Lee | |
| 5,893,862 A | 4/1999 | Pratt et al. | |
| 5,898,697 A | 4/1999 | Hurme et al. | |
| 5,921,999 A | 7/1999 | Dileo | |
| 5,925,056 A | 7/1999 | Thomas et al. | |
| 5,957,921 A | 9/1999 | Mirhashemi et al. | |
| 5,989,262 A | 11/1999 | Josephberg | |
| 6,036,688 A | 3/2000 | Edwards | |
| 6,059,792 A | 5/2000 | Josephberg | |
| 6,066,138 A | 5/2000 | Sheffer et al. | |
| 6,135,998 A | 10/2000 | Palanker | |
| 6,142,996 A | 11/2000 | Mirhashemi et al. | |
| 6,162,202 A | 12/2000 | Sicurelli et al. | |
| 6,165,190 A | 12/2000 | Nguyen | |
| 6,179,830 B1 | 1/2001 | Kokubu | |
| 6,203,518 B1 | 3/2001 | Anis et al. | |
| 6,217,598 B1 | 4/2001 | Berman et al. | |
| 6,241,721 B1 | 6/2001 | Cozean et al. | |
| 6,264,668 B1 | 7/2001 | Prywes | |
| 6,306,155 B1 | 10/2001 | Chandler et al. | |
| 6,379,370 B1 | 4/2002 | Feinsod | |
| 6,413,262 B2 | 7/2002 | Saishin et al. | |
| 6,440,103 B1 | 8/2002 | Hood et al. | |
| 6,503,263 B2 | 1/2003 | Adams | |
| 6,506,176 B1 | 1/2003 | Mittelstein et al. | |
| 6,544,254 B1 | 4/2003 | Bath | |
| 6,551,326 B1 * | 4/2003 | Van Heugten et al. | 606/113 |
| 6,575,929 B2 | 6/2003 | Sussman et al. | |
| 6,616,996 B1 | 9/2003 | Keith et al. | |
| 6,629,980 B1 | 10/2003 | Eibschitz-Tsimhoni | |
| 6,673,064 B1 | 1/2004 | Rentrop | |
| 6,764,439 B2 | 7/2004 | Schaaf et al. | |
| 6,979,328 B2 | 12/2005 | Baerveldt et al. | |
| 7,011,666 B2 | 3/2006 | Feinsod | |
| 7,135,009 B2 | 11/2006 | Tu et al. | |
| 2002/0007150 A1 | 1/2002 | Johnson | |
| 2002/0091402 A1 | 7/2002 | Feinsod | |
| 2002/0161365 A1 | 10/2002 | Martins | |
| 2004/0092982 A1 | 5/2004 | Sheffer | |
| 2004/0106929 A1 | 6/2004 | Masket | |
| 2004/0116950 A1 | 6/2004 | Eibschitz-Tsimhoni | |
| 2005/0054972 A1 | 3/2005 | Adams et al. | |
| 2005/0228419 A1 | 10/2005 | El-Mansoury | |
| 2006/0036270 A1 | 2/2006 | Terao | |
| 2006/0100617 A1 | 5/2006 | Boukhny | |
| 2006/0106370 A1 | 5/2006 | Baerveldt et al. | |
| 2006/0241580 A1 | 10/2006 | Mittelstein et al. | |
| 2006/0259053 A1 | 11/2006 | El-Mansoury | |
| 2007/0010812 A1 | 1/2007 | Mittelstein et al. | |
| 2007/0049957 A1 | 3/2007 | Benitez | |
| 2007/0060926 A1 | 3/2007 | Escaf | |
| 2007/0073275 A1 | 3/2007 | Conston et al. | |
| 2007/0078359 A1 | 4/2007 | Luloh et al. | |
| 2007/0191862 A1 | 8/2007 | Ellis | |
| 2007/0239156 A1 | 10/2007 | Palanker et al. | |
| 2007/0276420 A1 | 11/2007 | Sorensen et al. | |
| 2009/0216225 A1 | 8/2009 | Ben-Nun | |
| 2009/0287143 A1 | 11/2009 | Line | |
| 2009/0287233 A1 | 11/2009 | Huculak | |
| 2010/0057069 A1 | 3/2010 | Ben-Nun | |
| 2010/0094278 A1 * | 4/2010 | Jia et al. | 606/41 |
| 2010/0145447 A1 | 6/2010 | Jia et al. | |

FOREIGN PATENT DOCUMENTS

| | | | |
|---|---|---|---|
| DE | 3205959 A1 | 9/1983 | |
| DE | 3248101 A1 | 6/1984 | |
| DE | 3434930 A1 | 4/1986 | |
| DE | 8710541 U1 | 11/1987 | |
| DE | 197 40 530 A1 | 3/1990 | |
| DE | 4012882 A1 | 10/1991 | |
| DE | 9311879 U1 | 11/1993 | |
| DE | 19719549 A1 | 11/1998 | |
| DE | 19809510 A1 | 9/1999 | |
| DE | 10220253 A1 | 11/2002 | |
| EP | 183385 B1 | 3/1989 | |
| EP | 165657 B1 | 7/1989 | |
| EP | 0335714 A2 | 10/1989 | |
| EP | 358990 A1 | 3/1990 | |
| EP | 0228185 B1 | 7/1990 | |
| EP | 0355341 B1 | 10/1992 | |
| EP | 0537116 A1 | 4/1993 | |
| EP | 506618 B1 | 7/1995 | |
| EP | 0730848 A2 | 9/1996 | |
| EP | 0730848 A3 | 7/1997 | |
| EP | 0788802 A2 | 8/1997 | |
| EP | 0898947 A2 | 3/1999 | |
| EP | 0898947 A3 | 9/1999 | |

| | | |
|---|---|---|
| EP | 0730848 B1 | 4/2000 |
| EP | 0788802 A3 | 4/2000 |
| EP | 1010410 A1 | 6/2000 |
| EP | 0986328 A4 | 5/2001 |
| EP | 1095641 A1 | 5/2001 |
| EP | 0788802 B1 | 7/2006 |
| EP | 1809196 A4 | 3/2008 |
| ES | 2 103 635 | 9/1997 |
| FR | 2544979 A1 | 11/1984 |
| FR | 2588751 A1 | 4/1987 |
| FR | 2676355 | 11/1992 |
| FR | 2677244 A1 | 12/1992 |
| FR | 2702955 A1 | 9/1994 |
| FR | 2707872 A1 | 1/1995 |
| FR | 2830186 A1 | 4/2003 |
| FR | 2855745 A1 | 12/2004 |
| FR | 2855746 A1 | 12/2004 |
| FR | 2924924 A1 | 6/2009 |
| GB | 2247174 A | 2/1992 |
| GB | 2437252 A | 10/2007 |
| SU | 452338 | 12/1974 |
| SU | 1301400 A1 | 4/1987 |
| SU | 1395314 A1 | 5/1988 |
| SU | 1431752 A1 | 10/1988 |
| SU | 1440496 A1 | 11/1988 |
| SU | 1766403 A1 | 10/1992 |
| SU | 1790934 A1 | 1/1993 |
| SU | 1790935 A1 | 1/1993 |
| SU | 1148613 A1 | 4/1995 |
| WO | WO 86/02257 A1 | 4/1986 |
| WO | WO 93/01755 A1 | 2/1993 |
| WO | WO 95/08310 A1 | 3/1995 |
| WO | WO 96/06570 A1 | 3/1996 |
| WO | WO 97/26835 A1 | 7/1997 |
| WO | WO 97/30669 | 8/1997 |
| WO | WO 98/49945 A1 | 11/1998 |
| WO | WO 93/20765 A1 | 10/1999 |
| WO | WO 99/60936 A1 | 12/1999 |
| WO | WO 00/48540 A1 | 8/2000 |
| WO | WO 01/56519 A1 | 8/2001 |
| WO | WO 01/60266 A1 | 8/2001 |
| WO | WO 03/022174 | 3/2003 |
| WO | WO 03/022174 A3 | 3/2003 |
| WO | WO 03/039335 A2 | 5/2003 |
| WO | WO 03/039335 A3 | 5/2003 |
| WO | WO 03/045290 A1 | 6/2003 |
| WO | WO 2004/039295 | 5/2004 |
| WO | WO 2004/071312 A1 | 8/2004 |
| WO | WO 2006/052374 A2 | 5/2006 |
| WO | WO 2006/052374 A3 | 5/2006 |
| WO | WO 2006/109255 A1 | 10/2006 |
| WO | WO 2006/109290 A2 | 10/2006 |
| WO | WO 2006/117772 A1 | 11/2006 |
| WO | WO 2007/121485 A2 | 10/2007 |
| WO | WO 2008/080149 A1 | 7/2008 |
| WO | WO 2009/140414 A1 | 11/2009 |
| WO | WO 2009/153550 A1 | 12/2009 |
| WO | WO 2010/044988 A1 | 4/2010 |
| WO | WO 2010/068662 A1 | 6/2010 |
| WO | WO 2010/080859 A1 | 7/2010 |
| WO | WO 2010/141179 A1 | 12/2010 |
| WO | WO 2010/141181 A1 | 12/2010 |

OTHER PUBLICATIONS

Sussman, Glen et al., Capsularhexis Device with Flexible Heating Element having an Angled Transitional Neck, U.S. Appl. No. 12/477,175, filed Jun. 3, 2009, 32 pages.

International Searching Authority, International Preliminary Report on Patentability, PCT/US2005/036670, May 15, 2007, 4 pages.

Huculak, John C. et al., Capsularhexis Device Using Pulsed Electric Fields, U.S. Appl. No. 12/618,805, filed Nov. 16, 2009, 14 pages.

Jia, Guangyao, et al., Capsule Polishing Device and Method for Capsule Polishing, U.S. Appl. No. 12/777,820, filed May 11, 2010, 26 pages.

Jia, Guangyao, et al., Capsulotomy Repair Device and Method for Capsulotomy Repair, U.S. Appl. No. 12/754,119, filed Apr. 5, 2010, 40 pages.

Sussman, Glenn, et al., Small Gauge Ablation Probe for Glaucoma Surgery, U.S. Appl. No. 12/707,747, filed Feb. 18, 2010, 11 pages.

Karmel, Miriam, "Glaucoma Surgies: Trabectome and Canaloplasty Take the Stage," publication, May 2009, pp. 29-30, American Academy of Ophthalmology.

Lewandowski, Julia T., "Improving Ab Interno Trabeculotomy, A combination of advanced technology and insightful design may prompt surgeons to adopt a new technique for lowering IOP," article, Jul. 2007, 4 pages, Bryn Mawr Communications.

Abstract of SU1805938; Publication date Mar. 30, 1993; Priority date Mar. 11, 1991.

International Searching Authority, International Search Report, PCT/US2010/020295, May 17, 2010, 4 pages.

International Searching Authority, Written Opinion of the International Searching Authority, PCT/US2010/020295, May 17, 2010, 8 pages.

International Searching Authority, International Search Report, PCT/US2009/067305, Apr. 13, 2010, 4 pages.

International Searching Authority, Written Opinion of the International Searching Authority, PCT/US2009/067305, Apr. 13, 2010, 6 pages.

International Searching Authority, International Preliminary Report on Patentability, PCT/US2009/067305, Jun. 14, 2011, 7 pages.

International Searching Authority, International Preliminary Report on Patentability, PCT/US2010/020295, Jul. 12, 2011, 8 pp.

\* cited by examiner

CAPSULARHEXIS DEVICE WITH RETRACTABLE BIPOLAR ELECTRODES

TECHNICAL FIELD

The present invention relates generally to the field of cataract surgery and more particularly to methods and apparatus for performing a capsularhexis.

BACKGROUND

An accepted treatment for the treatment of cataracts is surgical removal of the lens and replacement of the lens function by an artificial intraocular lens (IOL). In the United States, the majority of cataractous lenses are removed by a surgical technique called phacoemulsification. Prior to removing the cataractous lens, an opening, or rhexis, must be made in the anterior capsule. During phacoemulsification, there is a great deal of tension on the cut edges of the anterior capsularhexis while the lens nucleus is emulsified. Accordingly, a continuous cut or tear (rhexis), without "tags," is a critical step in a safe and effective phacoemulsification procedure.

If the capsule is opened with numerous small capsular tears, the small tags that remain can lead to radial capsular tears which may extend into the posterior capsule. Such a radial tear constitutes a complication since it destabilizes the lens for further cataract removal and safe intraocular lens placement within the lens capsule later in the operation. Further, if the posterior capsule is punctured then the vitreous may gain access to the anterior chamber of the eye. If this happens, the vitreous must be removed by an additional procedure with special instruments. The loss of vitreous is also associated with an increased rate of subsequent retinal detachment and/or infection within the eye. Importantly, these complications are potentially blinding.

Conventional equipment used for phacoemulsification includes an ultrasonically driven handpiece with an attached cutting tip. In some of these handpieces, the operative part is a centrally located, hollow resonating bar or horn directly attached to a set of piezoelectric crystals. The crystals supply ultrasonic vibration for driving both the horn and the attached cutting tip during phacoemulsification.

Prior art devices and methods used for the capsularhexis procedure require a great deal of skill on the part of the surgeon to produce a continuous curvilinear capsular opening. This is due to the extreme difficulty in controlling the path of the cutting tip of the device. For example, a typical procedure begins with a capsular incision made with a cystotome, e.g., a cutting tip as described above. This incision is then coaxed into a circular or oval shape by pushing the leading edge of the incision in the capsule, using the cystotome as a wedge rather than in a cutting fashion. Alternatively, the initial capsular incision may be torn into a circular shape by grasping the leading edge with fine caliber forceps and advancing the cut. Either of these approaches involves a very challenging maneuver and the tearing motion can sometimes lead to an undesirable tear of the capsule toward the back of the lens, even in the most experienced hands.

Moreover, even if a smooth capsular opening without tags is ultimately produced, the size and/or position of the capsular opening may present a problem. For instance, a capsular opening that is too small can impede the safe removal of the lens nucleus and cortex and prevent proper intraocular lens insertion into the lens capsule. The additional stresses necessary to accomplish the operation with a small or misplaced capsular opening put the eye at risk for zonular and capsular breakage. Either of these complications will likely increase the length and complexity of the operation and may result in vitreous loss.

A continuous, properly positioned, and circular opening is thus highly desirable because it results in: (1) a significant reduction in radial tears and tags within the anterior capsule, (2) capsule integrity necessary for proper centering of a lens prosthesis; (3) safe and effective hydrodissection; and (4) safe use of capsular procedures on patients having poorly visualized capsules and/or small pupil openings. In addition, the capsularhexis should be properly dimensioned relative to the diameter of the IOL being implanted in order to reduce the chances of a secondary cataract, also called posterior capsule opacification ("PCO") and for use with proposed accommodative IOLs designs. Therefore, there is a continuing need for an improved device for performing an anterior chamber capsularhexis.

SUMMARY

Various embodiments of the present invention provide apparatus and corresponding methods of use for performing capsularhexis. In several embodiments, a capsularhexis device includes a loop-shaped cutting portion formed from flexible, superelastic metal strips separated by an insulating layer, and configured so that the cutting portion may be retracted into a tubular insertion cartridge for insertion into and removal from the eye, and extended from the insertion cartridge for the capsularhexis procedure. In its extended configuration, the cutting portion forms a cutting loop such that a free end of the cutting loop is proximate a connecting end of the cutting loop, with the connecting end joined to a shaft portion. The shaft portion extends into the insertion capsule, and is used to move the cutting portion in and out of the insertion cartridge.

Accordingly, an exemplary embodiment of a capsularhexis device according to some embodiments of the present invention includes a tubular insertion cartridge having a proximal end for engagement to a handpiece and a distal end for insertion into an eye, a shaft portion configured for longitudinal translation within the tubular insertion cartridge and comprising first and second electrical leads for electrical connection to an external power source, and a cutting portion having a connecting end, joined to the shaft portion, and a free end. The cutting portion comprises first and second superelastic electrode layers separated by an electrically insulating layer and electrically connected to the first and second electrical leads, respectively. The cutting portion is formed so that the capsularhexis device of this embodiment has an extended configuration, in which the cutting portion is external to the tubular insertion cartridge and forms a cutting loop with the free end proximate the connecting end and separated from the connecting end by a gap in the periphery of the cutting loop, as well as a retracted configuration, in which the cutting portion is contained substantially within the insertion cartridge such that the connecting end is farther from the distal end of the insertion cartridge than the remainder of the cutting portion.

In some embodiments, the superelastic electrode layers of the device's cutting portion are formed from a nickel titanium alloy. In these and other embodiments, the first and second superelastic electrode layers may comprise first and second elongated superelastic strips, each having a length approximately equal to the perimeter of the cutting loop, a thickness, and a height that exceeds the thickness, and be configured so that the first and second superelastic strips sandwich the insulation layer for at least a portion of the length and height of the superelastic strips. The electrically insulating layer may be formed from any suitable matter, including those materials commonly known as Parylene.

An exemplary method for utilizing a capsularhexis device, according to some embodiments of the invention, begins with the positioning of one end of a tubular insertion cartridge in or near the anterior chamber of an eye, the tubular insertion cartridge containing (a) at least a portion of a shaft configured for longitudinal translation within the tubular insertion cartridge and comprising first and second electrical leads for electrical connection to an external power source, and (b) substantially all of a cutting portion having a connecting end, joined to the shaft, and a free end, the cutting portion comprising first and second superelastic electrode layers separated by an electrically insulating layer and electrically connected to the first and second electrical leads. When the tip of the insertion cartridge is initially positioned in or near the eye, the cutting portion is in a retracted configuration such that the connecting end is farther from the distal end of the insertion cartridge than the remainder of the cutting portion. Using a handle that rigidly engages at least a portion of the shaft, the cutting portion is ejected from the tubular insertion cartridge, into the anterior chamber, so that the cutting portion forms a cutting loop with the free end proximate the connecting end and separated from the connecting end by a gap in the periphery of the cutting loop.

After the cutting loop is positioned in contact with the anterior lens capsule of the eye, a high-frequency electrical current is activated, causing the cutting portion to burn the lens capsule along the cutting loop. The cutting portion is then retracted into the tubular insertion cartridge, using the handle, before removal of the distal end of the tubular insertion cartridge from the eye.

Of course, those skilled in the art will appreciate that the present invention is not limited to the above features, advantages, contexts or examples, and will recognize additional features and advantages upon reading the following detailed description and upon viewing the accompanying drawings.

DETAILED DESCRIPTION

Figure 1:
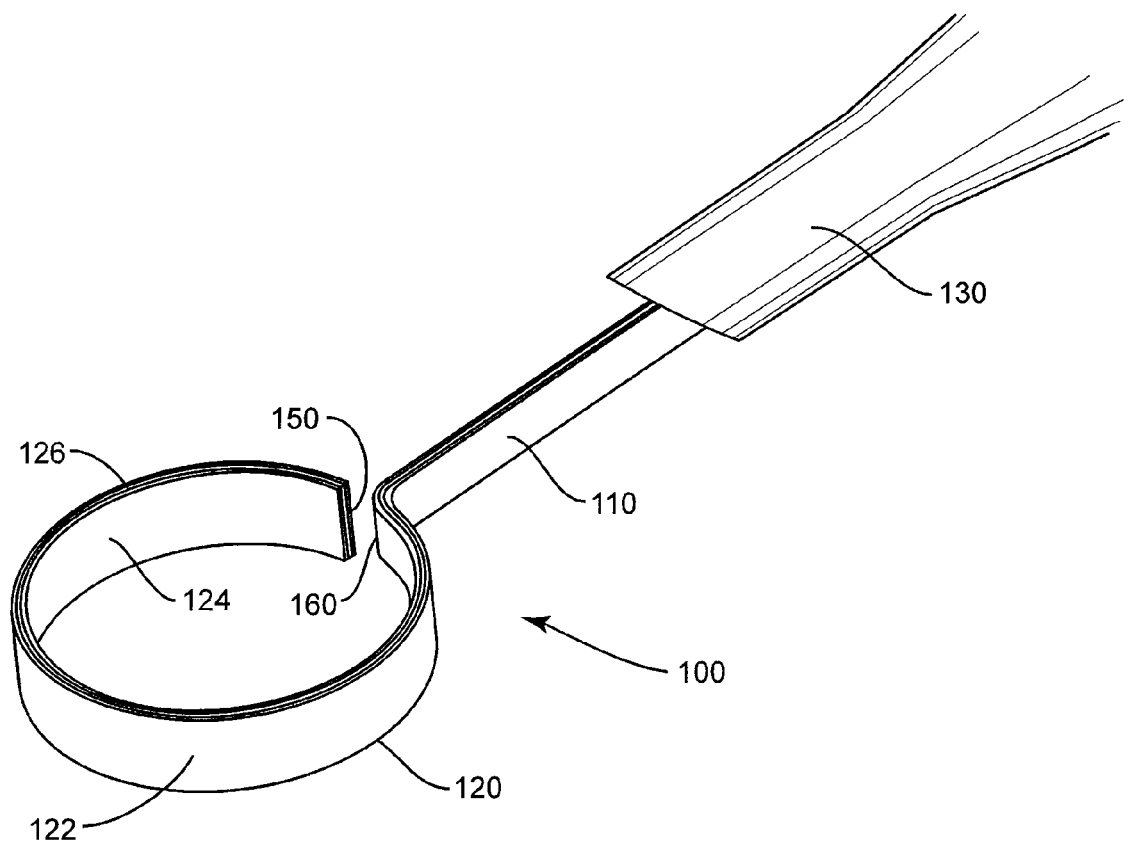
FIG. 1 is a perspective view of an exemplary capsularhexis device.

Various embodiments of the present invention provide apparatus and corresponding methods of use for performing capsularhexis. In particular, the present invention relates to a surgical instrument, a so-called capsularhexis device, which may be positioned within the anterior chamber of an eye through a small incision to perform capsularhexis, or capsulotomy. This procedure facilitates phacoemulsification of a cataractous lens and insertion of an artificial intraocular lens (IOL).

United States Patent Application Publication No. 2006/010061 describes a capsularhexis device comprising a circular, flexible ring made of an elastomer or an acrylic or thermoplastic material. Embedded within each of various embodiments of this flexible ring is either a resistance-heating element or a pair of bipolar electrodes, which are energized according to known techniques to produce localized heating on the anterior capsule, so as to define a weakened boundary for an easy detachment of the portion of the capsule within the circular ring.

According to several embodiments of the present invention, the flexible ring structure is replaced with a loop-shaped cutting portion formed from flexible, superelastic metal strips separated by an insulating layer, and configured so that the cutting portion may be retracted into a tubular insertion cartridge for insertion into and removal from the eye. A perspective view of one such embodiment is provided in FIG. 1, which shows a capsularhexis device 100 comprising a shaft portion 110, a cutting portion 120, and a tubular insertion cartridge 130. In the view pictured in FIG. 1, the capsularhexis device is in an extended configuration such that the cutting portion forms a cutting loop with the free end 150 of the cutting loop proximate a connecting end 160 of the cutting loop, with the connecting end joined to the shaft portion 110.

Because the cutting loop is not continuous, but has a small peripheral gap between the free end 150 and the connecting 160 of the cutting portion, the cutting portion can be retracted into the tubular insertion cartridge 130. In the retracted configuration, the distal end of the insertion cartridge, which has a much smaller cross-sectional profile than the extended cutting loop, can be inserted into a very small incision in the eye, e.g., an incision less than 2 millimeters in length.

Figure 2:
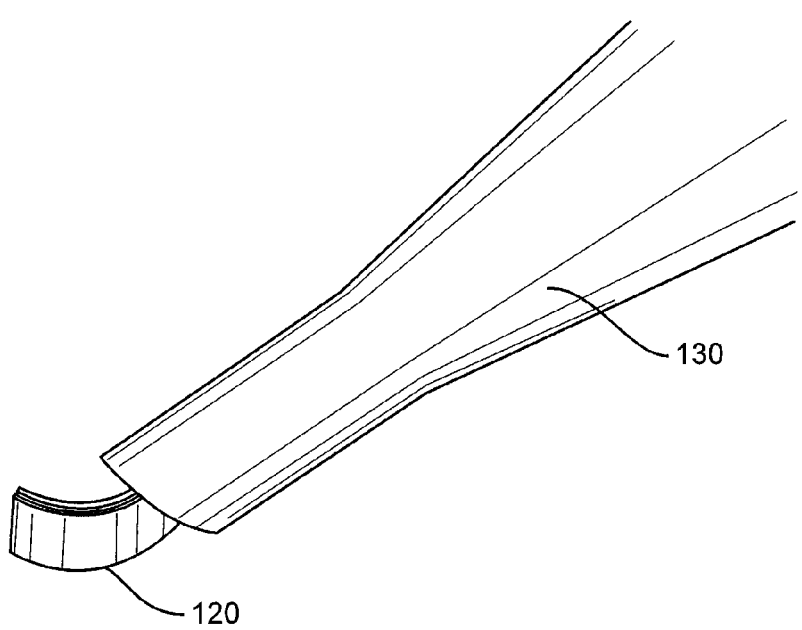
FIG. 2 illustrates the capsularhexis device of FIG. 1, with the device's cutting portion partially retracted into a tubular insertion cartridge.
Figure 3:
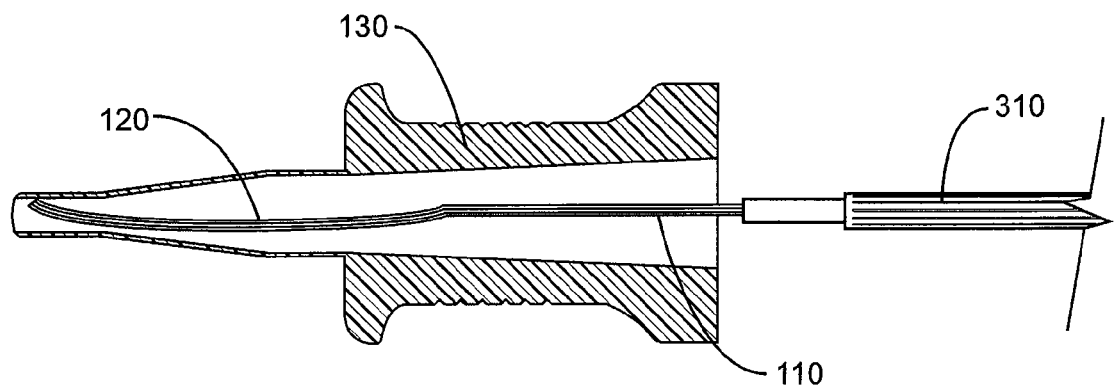
FIG. 3 is a cross-sectional view of an exemplary capsularhexis device retracted into a tubular insertion cartridge.

This retracted configuration is illustrated in FIG. 2, in which the cutting portion 120 has been almost entirely retracted into the insertion cartridge 130, with only a small portion of the cutting portion 120 protruding from the distal end of the tubular insertion cartridge. FIG. 3 provides a cross-sectional view of an exemplary capsularhexis device in a fully retracted configuration; in this view the cutting portion 120 has been retracted, using the shaft portion 120 and a handle 130 that rigidly engages the shaft portion 120, and is completely contained within the tubular insertion cartridge 130. In this configuration, the free end 150 of the cutting portion is near the distal end of the insertion cartridge 130, and the connecting end 160 is retracted deep into the cartridge, so that the connecting end 160 is farther from the distal end of the insertion cartridge than the remainder of the cutting portion.

The cutting portion 120 regains its loop shape upon extension from the insertion cartridge 130 because it is formed from materials having superelastic properties. Referring once more to FIG. 1, the cutting portion 120 of the pictured capsularhexis device 100 includes two superelastic electrode layers 122 and 124, which are separated by a thin, electrically insulating layer 126 (which may be any suitable material such as Parylene). In particular, the electrode layers 122 and 124 may be formed from a nickel titanium alloy, commonly known as Nitinol, which exhibits superelastic and shape memory properties. Because it is superelastic (which term is intended herein as a synonym for the somewhat more technically precise term "pseudoelastic"), an object made from Nitinol can withstand a significant amount of deformation when a load is applied and return to its original shape when the load is removed. (Those skilled in the art will appreciate that this property is distinct from, although related to, "shape memory", which refers to a property exhibited by some materials in which an object that is deformed while below the material's transformation temperature returns to its former shape when warmed to above the transformation temperature. Nitinol exhibits both properties; superelasticity is exhibited above the transformation temperature.) Accordingly, a cutting portion 120 formed from Nitinol electrodes in the extended, loop-shaped configuration of FIG. 1 (e.g., by forming appropriately dimensioned strips into the desired shape and heat-treating at a temperature in the 500° C. range) can be deformed into the retracted configuration pictured in FIGS. 2 and 3, and return to its previous loop shape when extended again.

Because Nitinol is also electrically conductive, the Nitinol layers can serve as bipolar electrodes for applying a high-frequency electrical current to the lens capsule. The current is supplied to the electrodes 122 and 124 through electrical leads passing through the shaft portion 110 for electrical connection to an external power source (not shown). In FIG. 1, the layers that form the electrodes 122 and 124 continue through the visible portion of the shaft portion 110, thus serving as electrical leads for supplying the high-frequency current to the cutting portion 120. In some embodiments, the Nitinol layers may extend throughout the shaft portion, with an electrical connector, soldered wire leads, or the like, attached to the far end of the shaft portion for supplying the high-frequency current from the external power source. In others, the Nitinol layers may be terminated at various points along the shaft portion, and connected to conventional wire leads, metallic strips of another electrically conductive material, or the like.

Figure 4:
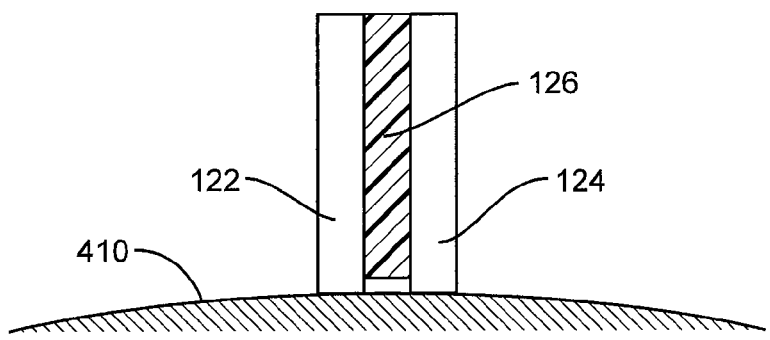
FIG. 4 is a cross sectional view of the cutting portion of an exemplary capsularhexis device.

FIG. 4 shows a cross-sectional view of the cutting portion 120 applied against a portion of the anterior capsule 410 of an eye. The electrodes 122 and 124 define the boundaries of the portion of the lens capsule that is cauterized by the high-frequency current when the electrodes are energized. When applied against the anterior lens capsule 410, the spacing between the electrodes 124 and 126 defines a gap across which the high-frequency current flows when the electrodes are energized, burning the intervening lens capsule tissue and weakening it, so that a roughly circular portion of the lens capsule can be easily removed, using forceps. The basic principles of such electro-surgery, which may involve, for example, frequencies of greater than 100 kHz, are well known to those skilled to the art; accordingly, the details of such procedures, which are not necessary to a complete understanding of the present invention, are not provided herein.

Those skilled in the art will appreciate that other materials that are electrically conductive and superelastic may be used instead of Nitinol in some embodiments of the invention. Those skilled in the art will further appreciate that the general shape and/or cross-section of the cutting portion 120 and shaft 110 may vary from that pictured in FIGS. 1-4. For instance, the embodiment pictured in these figures includes a cutting portion formed from elongated superelastic strips with rectangular cross sections that sandwich a very thin electrically insulating layer 126, with each strip having a length approximately equal to the perimeter of the of the cutting loop, a relatively small thickness, compared to the diameter of the loop, and a height that is several times the thickness. Other embodiments might employ one or more strips having height and thickness dimensions that are closer to being equal. In these or other embodiments, one or more of the planar surfaces of FIGS. 1-2 might be rounded instead. Although a circular capsularhexis is generally preferred, to reduce the possibility of undesirable tearing when the cut portion of the lens is removed, the cutting loop formed by the cutting portion 120 need not be perfectly circular. Similarly, when the device is in its extended configuration the gap in the periphery of the cutting loop between the free end 150 and the connecting end 160 of the cutting portion 120 should preferably be relatively small, compared to the overall dimensions of the loop, or even touching (e.g., separated only by an insulating layer). However, larger gaps may be acceptable, in some embodiments.

The details of the tubular insertion cartridge 130 and the handle 310 may also from one embodiment to another. In the embodiment pictured in FIG. 3, handle 310 is a flat or cylindrical tube that rigidly engages a portion of the shaft section. Handle 310 may thus be used to insert the cutting portion 120 into the eye during the capsularhexis procedure and to retract the cutting portion 120 afterwards, as will be discussed in further detail below. The handle 310, which may be made from an inexpensive material such as a thermoplastic, may also contain electrical connectors and/or connecting wires so that the cutting portion 120 may be selectively connected to a high-frequency power source for the capsularhexis procedure. In some embodiments, the handle 310, shaft portion 110, and cutting portion 120 form a disposable unit that can be selectively connected during use to a handpiece or other apparatus that can supply electrical current; in other embodiments the assembly comprising the handle 310, shaft portion 110, and cutting portion 120 may be cleaned and re-used several times.

Similarly, the insertion cartridge 130 in some embodiments is a disposable polymeric component, while in other embodiments the insertion cartridge 130 may be re-usable and/or may be an integral part of a re-usable capsularhexis handpiece. In any case, the tubular insertion cartridge 130 is generally adapted to accommodate a longitudinally translating shaft portion 110 and a retracted cutting portion 120, as shown in FIG. 3, so that the cutting portion 120 may be extended from the distal end of the tubular insertion cartridge 130, into the anterior chamber of an eye, for the capsularhexis procedure. The proximal end of the insertion cartridge engages with the rest of a capsularhexis handpiece, accommodating longitudinal translation of the shaft portion 110 and/or handle 310, to eject and retract the cutting portion 120. Although a mechanism for moving the handle 310 is not shown in FIG. 3, those skilled in the art will appreciate that various manual mechanisms (e.g., a tab extending from the handle) or automated mechanisms (e.g., a motorized linear actuator) are possible.

Figure 5A:
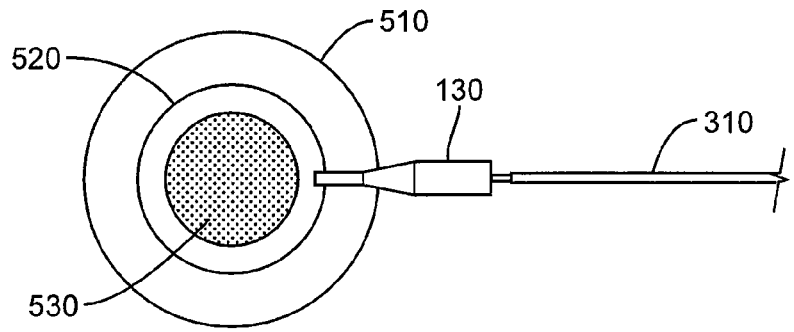
FIGS. 5A-5D illustrate the insertion and removal of a capsularhexis device during cataract surgery.

FIGS. 5A-5D illustrate the insertion of the cutting portion 120 into an eye 510, using an insertion cartridge 130. Prior to the procedure, the cutting portion 120 has been withdrawn into the insertion cartridge, so that the cutting portion 120 is contained entirely within the cartridge 130. Thus, the leading tip of the apparatus can be inserted into the anterior chamber 520 of the eye 510, as shown in FIG. 5A, through a small incision.

Figure 5B:
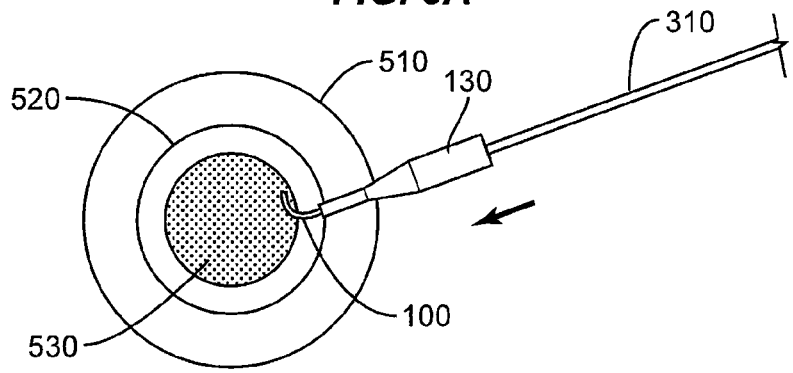
Figure 5C:
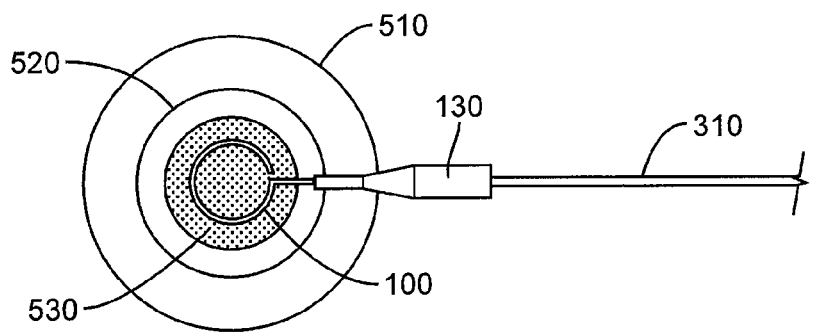
Figure 5D:
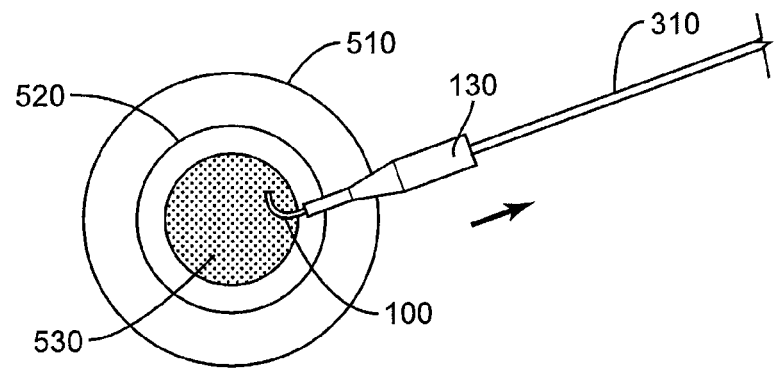

Using handle 310, the retracted cutting portion 120 is pushed through the cartridge 130, as shown in FIG. 5B, until it is completely within the anterior chamber 520, as shown in FIG. 5C. When ejected from the insertion cartridge 130 into its extended configuration, the cutting portion 120 regains its pre-determined shape, i.e., forming a cutting loop, as shown in FIG. 5C, and is then positioned against the capsule 530. The cutting portion 120 is then energized, e.g., with a short pulse or series of pulses of high-frequency current. As discussed above, this energizing of the bipolar electrodes sears the capsule 530, effectively creating a smooth continuous cut on the capsule. The cutting portion 120 may then be retracted into the insertion cartridge 130, as shown in FIG. 5D, and then removed from the eye 510. The cut portion of the capsule is then readily removed using a conventional surgical instrument, such as forceps.

Figure 6:
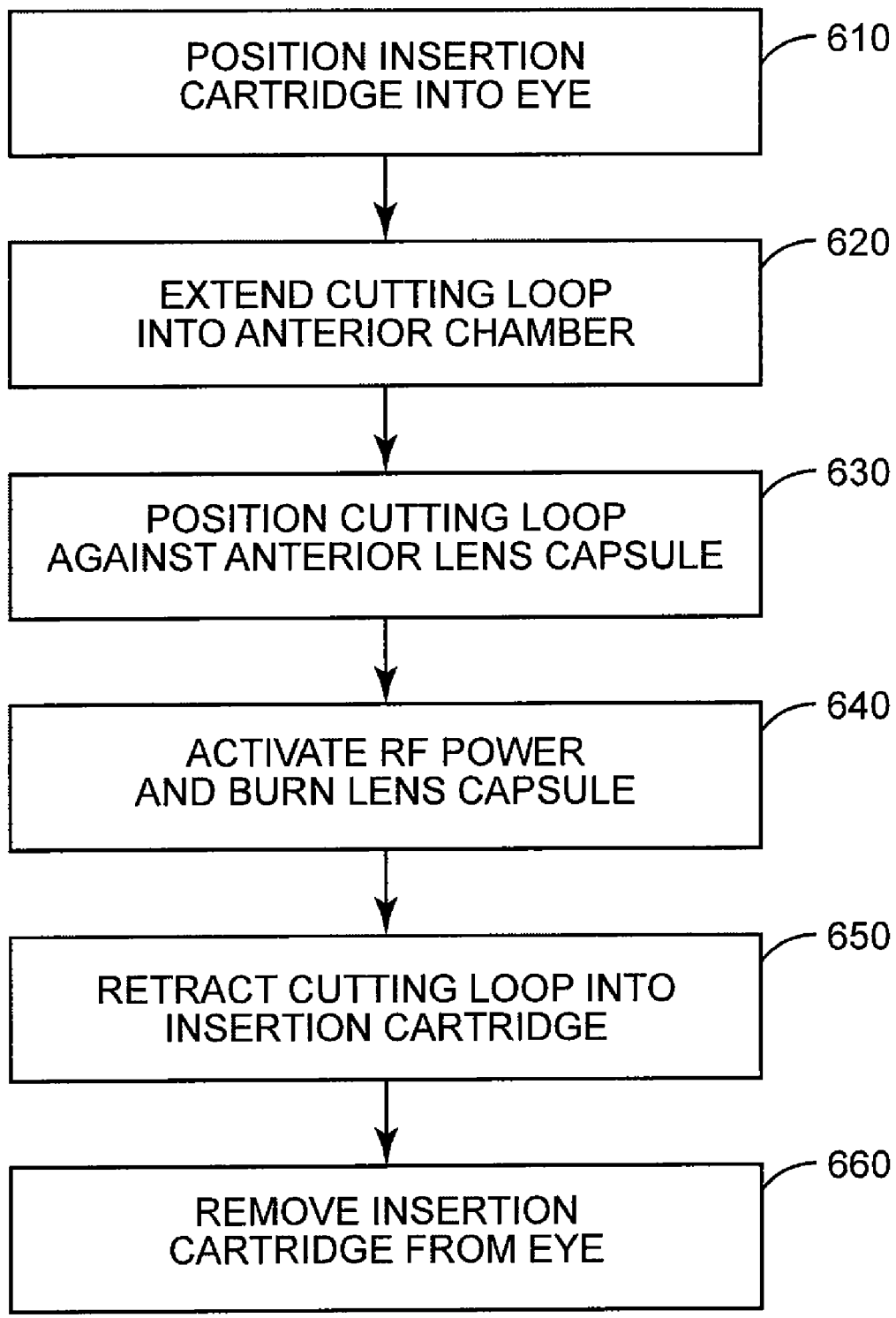
FIG. 6 is a process flow diagram illustrating an exemplary method for utilizing a capsularhexis device.

With the above-described device configurations in mind, those skilled in the art will appreciate that FIG. 6 illustrates a method for utilizing a capsularhexis device according to some embodiments of the present invention. The illustrated procedure begins with the positioning of an insertion cartridge into the eye, as illustrated at block 610, and the extension of the cutting portion 120 into the anterior chamber of the eye, as shown at block 620. Because the cutting portion 120 described herein is effectively collapsed when in its retracted configuration, the insertion cartridge 130 may be dimensioned to fit through an incision that is considerably smaller than the expanded diameter of the cutting loop formed by the extended cutting portion 120.

Once the cutting portion 120 is ejected into the eye, the cutting loop may be positioned against the anterior lens capsule, as shown at block 630. After the cutting loop is correctly positioned against the capsule, it is energized by the application of high-frequency electrical current, as shown at block 640, so that the lens capsule is "burned" along the curve formed by the cutting loop. Once the burning of the capsule is complete, the cutting portion 120 may be retracted into the insertion cartridge, as shown at block 650, and removed from the eye, as shown at block 660.

The preceding description of various embodiments of a capsularhexis device and methods for utilizing a capsularhexis device was given for purposes of illustration and example. Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A capsularhexis device, comprising:
    a tubular insertion cartridge having a proximal end for engagement to a handpiece and a distal end for insertion into an eye;
    a shaft portion configured for longitudinal translation within the tubular insertion cartridge and comprising first and second electrical leads for electrical connection to an external power source; and
    a cutting portion having a connecting end, joined to the shaft portion, and a free end, the cutting portion comprising first and second superelastic electrode layers separated by an electrically insulating layer and electrically connected to the first and second electrical leads, respectively;
    wherein the capsularhexis device has an extended configuration, in which the cutting portion is external to the tubular insertion cartridge and forms a cutting loop with a gap in a periphery of the cutting loop, and a retracted configuration, in which the cutting portion is contained substantially within the insertion cartridge such that the connecting end is farther from the distal end of the insertion cartridge than a remainder of the cutting portion;
    wherein the first and second superelastic electrode layers comprise first and second elongated superelastic strips, each having a length approximately equal to or greater than the perimeter of the cutting loop, a thickness, and a height; and
    wherein the first and second superelastic strips sandwich the insulation layer for at least a portion of the length and height of the superelastic strips.

2. The capsularhexis device of claim 1, wherein the superelastic electrode layers are formed from a nickel titanium alloy.

3. The capsularhexis device of claim 1, wherein the height of the first and second superelastic electrode layers exceeds the thickness of the first and second superelastic electrode layers.

4. The capsularhexis device of claim 1, wherein the distal end of the tubular insertion cartridge is configured to be inserted into an incision less than 2 millimeters in length when the capsulorhexis device is in the retracted configuration.

5. The capsularhexis device of claim 1, wherein the first and second superelastic electrode layers are configured to cauterize a lens capsule of the eye by applying a high-frequency electrical current.

6. The capsularhexis device of claim 1, wherein the first superelastic electrode layer has a rectangular cross section.

7. The capsularhexis device of claim 1, wherein the height of the first and second superelastic electrode layers approximately equals the thickness of the first and second superelastic electrode layers.

8. The capsularhexis device of claim 1, wherein the cutting loop is approximately circular.

9. The capsularhexis device of claim 1, wherein the cutting loop is approximately circular.

10. The capsularhexis device of claim 1, wherein the gap in the periphery of the cutting loop is spanned by an insulating layer.

11. The capsularhexis device of claim 1, wherein the cutting loop is configured to be placed against an anterior lens capsule in the eye.

* * * * *